United States Patent
Haiminen et al.

(10) Patent No.: US 10,460,832 B2
(45) Date of Patent: *Oct. 29, 2019

(54) EXACT HAPLOTYPE RECONSTRUCTION OF F2 POPULATIONS

(71) Applicant: International Business Machines Corporation, Armonk, NY (US)

(72) Inventors: Niina S. Haiminen, White Plains, NY (US); Laxmi P. Parida, Mohegan Lake, NY (US); Filippo Utro, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 532 days.

This patent is subject to a terminal disclaimer.

(21) Appl. No.: 13/761,730

(22) Filed: Feb. 7, 2013

(65) Prior Publication Data

US 2013/0345987 A1  Dec. 26, 2013

Related U.S. Application Data

(63) Continuation of application No. 13/529,476, filed on Jun. 21, 2012.

(51) Int. Cl.
*G16B 45/00* (2019.01)
*G06F 17/16* (2006.01)
*G16B 20/00* (2019.01)

(52) U.S. Cl.
CPC ............ *G16B 45/00* (2019.02); *G06F 17/16* (2013.01); *G16B 20/00* (2019.02)

(58) Field of Classification Search
None
See application file for complete search history.

(56) References Cited

U.S. PATENT DOCUMENTS

| | | | |
|---|---|---|---|
| 6,931,326 | B1 | 8/2005 | Judson et al. |
| 7,043,461 | B2 * | 5/2006 | Kehder et al. ............ 706/13 |
| 2004/0138824 | A1 | 7/2004 | Da et al. |
| 2007/0243539 | A1 * | 10/2007 | Ghosh et al. .............. 435/6 |
| 2008/0125978 | A1 | 5/2008 | Robson et al. |
| 2008/0243398 | A1 | 10/2008 | Rabinowitz et al. |
| 2010/0256917 | A1 | 10/2010 | McVean et al. |
| 2014/0136161 | A1 | 5/2014 | Haiminen et al. |
| 2014/0136166 | A1 | 5/2014 | Haiminen et al. |

OTHER PUBLICATIONS

Mitchell et al 'Power of variance component linkage analysis to detect epistatsis' vol. 14 issue 6 pare 1017-1022 (1997).*

L. Javed et al., "Recombinomics: population genomics from a recombination perspective," Proceedings of the Third C* Conference on Computer Science and Software Engineering, C3S2E '10, 2010, pp. 129-137.

B. L. Browning et al., "Simultaneous genotype calling and haplotype phasing improves genotype accuracy and reduces False-Positive associations for genome-wide association studies," The American Journal of Human Genetics, vol. 85, No. 6, Dec. 2009, pp. 847-861.

S. R. Browning et al., "Rapid and accurate haplotype phasing and missing-data inference for whole-genome association studies by use of localized haplotype clustering," The American Journal of Human Genetics, vol. 81, No. 5, Nov. 2007, pp. 1084-1097.

S. Purcell et al., "PLINK: a tool set for whole-genome association and population-based linkage analyses," The American Journal of Human Genetics, vol. 81, No. 3, Nov. 2007, pp. 559-575.

P. Scheet et al., "A fast and flexible statistical model for Large-Scale population genotype data: Applications to inferring missing genotypes and haplotypic phase," The American Journal of Human Genetics, vol. 78, No. 4, Apr. 2006, pp. 629-644.

B. V. Halldórsson et al., "A survey of computational methods for determining haplotypes," in Computational Methods for SNPs and Haplotype Inference, vol. 2983 of Lecture Notes in Computer Science, 2004, Springer Berlin/Heidelberg, pp. 26-47.

M. Stephens et al., "A Comparison of Bayesian Methods for Haplotype Reconstruction from Population Genotype Data," The American Journal of Human Genetics, vol. 73, No. 5, Nov. 2003 pp. 1162-1169.

Final Office Action dated Aug. 13, 2015 received for U.S. Appl. No. 13/529,476.

Final Office Action dated Mar. 17, 2016 received for U.S. Appl. No. 13/529,476.

Non-Final Office Action dated May 19, 2016 received for U.S. Appl. No. 13/529,476.

* cited by examiner

*Primary Examiner* — Joseph Woitach
(74) *Attorney, Agent, or Firm* — Fleit Gibbons Gutman Bongini Bianco PL; Thomas S. Grzesik

(57) ABSTRACT

A system for reconstructing haplotypes from genotype data includes a memory, a processor, and a reconstruction module. The reconstruction module is configured to access a set of progeny genotype data including n progenies encoded with m genetic markers. A first set of parent haplotypes associated with a first parent of the n progenies and a second set of parent haplotypes associated with a second parent of the n progenies are identified based on at least the set of progeny genotype data. An agglomerate data structure including a collection of sets of haplotype sequences characterizing the n progenies is constructed based on the set of progeny genotype data and the first and second sets of parent haplotypes. Each set of haplotype sequences includes a number of crossovers equal to a total minimum number of observable crossovers in the n progenies.

20 Claims, 6 Drawing Sheets

| | | | | | | | | | |
|---|---|---|---|---|---|---|---|---|---|
| TC | TC | TC | TC | AG | AA | AA | CC | CC | ⋯ |
| TT | TT | TT | TT | AG | AA | AA | CC | AC | ⋯ |
| TT | TT | TT | TT | AG | AA | AA | CC | AC | ⋯ |
| TC | TC | TC | TC | AG | AA | AA | CC | CC | ⋯ |
| TC | TC | TC | TT | GG | AC | AG | CC | AA | ⋯ |
| ⋮ | ⋮ | ⋮ | ⋮ | ⋮ | ⋮ | ⋮ | ⋮ | ⋮ | |

FIG. 3

| | | | | | | | | |
|---|---|---|---|---|---|---|---|---|
| $V^a(0)$ | X | X | X | H | x | x | x | h | X | ⋯ |
| $V^a(1)$ | X | X | X | H | x | x | x | h | X | ⋯ |
| $V^b(0)$ | X | X | X | x' | H | H | H | h | X | ⋯ |
| $V^b(1)$ | X | X | X | x' | H | H | H | h | X | ⋯ |

| | |
|---|---|
| X | heterozygous in both parents |
| x or x' | heterozygous in only one parent |
| H | homozygous in only one parent |
| h | homozygous in both of the parents |

EXACT HAPLOTYPE RECONSTRUCTION OF F2 POPULATIONS

CROSS-REFERENCE TO RELATED APPLICATIONS

This application is a continuation of and claims priority from U.S. patent application Ser. No. 13/529,476, filed on Jun. 21, 2012, the entire disclosure of which is herein incorporated by reference.

BACKGROUND

The present invention generally relates to the field of computational biology, and more particularly relates to exact haplotype reconstruction of F2 populations.

An important question when studying the genetics of an individual is that of determining its haplotype organization, i.e., determining the parental origin of each region in the individual's genome. When diploid organisms reproduce, crossovers frequently occur during meiosis. Therefore, progenies do not always receive complete copies of their parents' chromosomes. Instead, the genetic material inherited from a parent is often a combination of segments from the two chromosomes present in that parent, i.e. a combination of the two haplotypes of the parent (and similarly for material inherited from the other parent).

In practice, haplotypes are often constructed from genotype data. The genotype of an individual represents a sequence of unordered pairs of allele values associated with the diploid genome. Genotypes are often sampled as sequences of SNP (single-nucleotide polymorphism) marker values at locations spread across the genome. Determining the haplotypes for an individual at a given marker involves assigning each of the two unordered allele values to the correct parent from which it was inherited, and more precisely, to the correct haplotype of that parent.

Haplotype studies are extensively applied in the field of population genetics. For example, one can reconstruct so called ancestral founder haplotypes and represent the current population as a mosaic of those sequences. In another example, when the diploid parental genomes are known, one can separate them into haplotypes and represent the progenies as a mosaic of those haplotypes. The challenges of such applications include a) accurately collecting genomic data on the studied population, and b) constructing efficient and accurate algorithms for solving the associated combinatorially challenging problems.

BRIEF SUMMARY

In one embodiment, a system for reconstructing haplotypes from genotype data is disclosed. The system comprises a memory and a process communicatively coupled to the memory. A reconstruction module is communicatively coupled to the memory and processor. The reconstruction module is configured to perform a method comprising accessing a set of progeny genotype data comprising n progenies encoded with m genetic markers. A first set of parent haplotypes associated with a first parent of the n progenies and a second set of parent haplotypes associated with a second parent of the n progenies are identified based on at least the set of progeny genotype data. A total minimum number of observable crossovers in the n progenies is determined. An agglomerate data structure comprising a collection of sets of haplotype sequences characterizing the n progenies is constructed based on the set of progeny genotype data and the first and second sets of parent haplotypes. Each set of haplotype sequences includes a number of crossovers equal to the total minimum number of observable crossovers in the n progenies.

In another embodiment, a computer program storage product for reconstructing haplotypes from genotype data is disclosed. The computer program storage product comprises instructions configured to perform a method. The method comprises accessing a set of progeny genotype data comprising n progenies encoded with m genetic markers. Each of the m genetic markers comprises two values per individual. Also, a combination of each of the m genetic markers associated with a progeny represents a genotype sequence of the progeny. A first set of parent haplotypes associated with a first parent of the n progenies and a second set of parent haplotypes associated with a second parent of the n progenies are identified based on at least the set of progeny genotype data. A total minimum number of observable crossovers in the n progenies is determined. An agglomerate data structure comprising a collection of sets of haplotype sequences characterizing the n progenies in terms of the first and second sets of parent haplotypes is constructed based on the set of progeny genotype data and the first and second sets of parent haplotypes. Each set of progeny haplotype sequences comprises a number of crossovers equal to the total minimum number of observable crossovers in the n progenies.

BRIEF DESCRIPTION OF THE SEVERAL VIEWS OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present invention, in which:

FIG. 3 illustrates one example of a matrix comprising a display of dinucleotide data according to one embodiment of the present invention;

FIG. 4 illustrates one example of parental encodings based on genotype data partially shown in FIG. 3 according to one embodiment of the present invention;

DETAILED DESCRIPTION

Haplotype information can be extremely useful in determining the specific form of a gene that is associated with a phenotype such as disease susceptibility. Haplotype information can be used first to determine the genomic location of a gene associated with the phenotype and second to determine the exact forms (haplotypes) that are associated with the phenotype at that location. Haplotype information is also useful in the field of population genetics.

One problem with constructing haplotype information from genotype data is that given genotypes of n progenies on m loci, the general problem of constructing haplotypes from genotypes is NP complete under different models such as parsimony, maximum likelihood, and phylogeny. However, the duality of bi-allelic markers and F2 progenies (i.e., two founder sequences per haplotype), as is the case with plant breeding data, provides a compelling combinatoric puzzle. Rather than tweak generic software to adapt to the stringent conditions, embodiments of the present invention solve this problem more accurately and efficiently in a model-free setting. This is achieved, in one embodiment, by seeking out a mathematical lower bound on the number of crossovers in the data. The focus is not just on a maximum likely or a most parsimonious solution, but on an "agglomerate" of all (equally-likely) feasible solutions. All the computations including the agglomerate can be achieved in linear time. Also, the level of preciseness of the solution is such that it not only permits study of statistical trends, such as haplotype distributions along the chromosome, association with QTLs and so on, but can also help hand-pick individual recombinants that can be independently confirmed through resequencing for further experimentations.

Operating Environment

Figure 1:
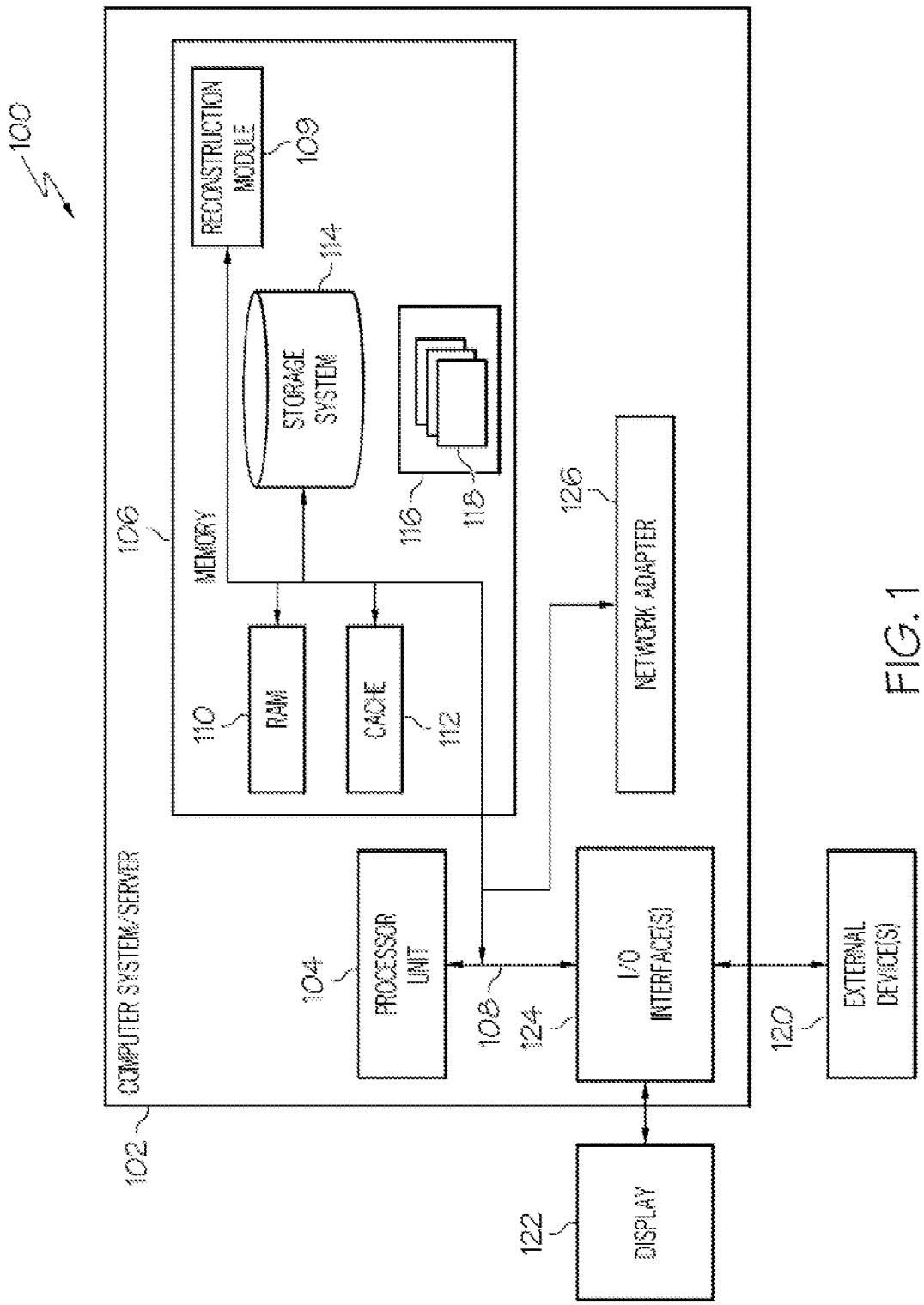
FIG. 1 is a block diagram illustrating one example of an operating environment according to one embodiment of the present invention.

FIG. 1 illustrates a general overview of one operating environment 100 for reconstructing haplotypes according to one embodiment of the present invention. In particular, FIG. 1 illustrates an information processing system 102 that can be utilized in embodiments of the present invention. The information processing system 102 shown in FIG. 1 is only one example of a suitable system and is not intended to limit the scope of use or functionality of embodiments of the present invention described above. The information processing system 102 of FIG. 1 is capable of implementing and/or performing any of the functionality set forth above. Any suitably configured processing system can be used as the information processing system 102 in embodiments of the present invention.

As illustrated in FIG. 1, the information processing system 102 is in the form of a general-purpose computing device. The components of the information processing system 102 can include, but are not limited to, one or more processors or processing units 104, a system memory 106, and a bus 108 that couples various system components including the system memory 106 to the processor 104.

The bus 108 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The system memory 106, in one embodiment, comprises a reconstruction module 109 configured to reconstruct haplotypes of F2 populations. As will be discussed in greater detail below, the reconstruction module 109 takes as input a set of gentoypes of n F2 progenies on m markers. Based on this input the reconstruction module 109 extracts all the equally-likely haplotypes of the progenies to produce an agglomerate structure. This agglomerate structure can be utilized by the reconstruction module 109 to compute the parameters of the distribution of each individual crossover, which makes further analysis of haplotype frequencies both more informative as well as accurate. Additionally, the reconstruction module 109 can visualize the solutions (e.g., a collection of haplotype sequences satisfying a lower bound) as mosaics of the ancestor haplotypes. It should be noted that even though FIG. 1 shows the reconstruction module 109 residing in the main memory, the reconstruction module 109 can reside within the processor 104, be a separate hardware component, and/or be distributed across a plurality of information processing systems and/or processors.

The system memory 106 can include computer system readable media in the form of volatile memory, such as random access memory (RAM) 110 and/or cache memory 112. The information processing system 102 can further include other removable/non-removable, volatile/non-volatile computer system storage media. By way of example only, a storage system 114 can be provided for reading from and writing to a non-removable or removable, non-volatile media such as one or more solid state disks and/or magnetic media (typically called a "hard drive"). A magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 108 by one or more data media interfaces. The memory 106 can include at least one program product having a set of program modules that are configured to carry out the functions of an embodiment of the present invention.

Program/utility 116, having a set of program modules 118, may be stored in memory 106 by way of example, and not limitation, as well as an operating system, one or more application programs, other program modules, and program data. Each of the operating system, one or more application programs, other program modules, and program data or some combination thereof, may include an implementation of a networking environment. Program modules 118 generally carry out the functions and/or methodologies of embodiments of the present invention.

The information processing system 102 can also communicate with one or more external devices 120 such as a keyboard, a pointing device, a display 122, etc.; one or more devices that enable a user to interact with the information processing system 102; and/or any devices (e.g., network card, modem, etc.) that enable computer system/server 102 to communicate with one or more other computing devices. Such communication can occur via I/O interfaces 124. Still yet, the information processing system 102 can communicate with one or more networks such as a local area network (LAN), a general wide area network (WAN), and/or a public network (e.g., the Internet) via network adapter 126. As depicted, the network adapter 126 communicates with the other components of information processing system 102 via the bus 108. Other hardware and/or software components can also be used in conjunction with the information processing system 102. Examples include, but are not limited to: microcode, device drivers, redundant processing units, external disk drive arrays, RAID systems, tape drives, and data archival storage systems.

Haplotype Reconstruction

Figure 2:
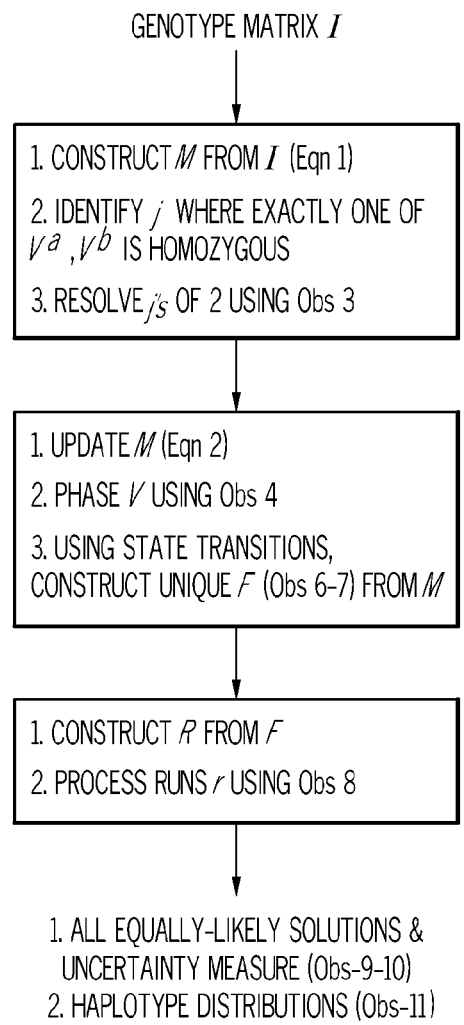
FIG. 2 is an illustrational flow of an overall process for reconstructing haplotypes from genotype data according to one embodiment of the present invention.

As discussed above, the reconstruction module 109 reconstructs haplotypes of F2 (the second filial generation resulting from the cross-mating or self-mating of a first filial generation) progenies in a set of genotypes. FIG. 2 shows an overview of this haplotype reconstruction process. For example, FIG. 2 shows that the reconstruction module 109 receives a genotype matrix $\mathcal{I}$ as input. The reconstruction module 109 constructs haplotype matrices M from $\mathcal{I}$ and identifies the column j where exactly one of parent haplotypes $V^a$ and $V^b$ is homozygous (i.e., two identical alleles exist at a given locus). The identified columns are resolved (based on Observation 3 discussed below) to identify a set of markers with exactly one heterozygous (i.e., two different alleles exist at a given locus) parent p. The matrices M are updated (based on EQ. 2 discussed below) and each of the parental haplotype pairs $V^a$ and $V^b$ are phased (based on Observation 4 discussed below), where phasing denotes resolving the haplotypes. State transitions are used to construct a unique matrices F from matrices M (based on observations 6 and 7 discussed below). An agglomerate structure R (i.e., matrices $R^a$ and $R^b$) is created from matrices F and runs r in R are processed (based on observation 8 discussed below). The reconstruction module 109 then outputs all equally-likely solutions (a collection of haplotype sequence sets, comprising each progeny in the genotype data, that satisfy a lower bound) based on observations 9 and 10 discussed below. The reconstruction module 109 also outputs haplotype distributions (based on observation 11 discussed below).

The following is a more detailed discussion on the haplotype reconstruction process shown in FIG. 2. In one embodiment the set of genotype data is structured within a matrix $\mathcal{I}$, as shown in FIG. 3. Matrix $\mathcal{I}$ is an n×m matrix that encodes n progenies with m markers. Each row i, $1 \leq i \leq n$, represents a progeny and each column j, $1 \leq j \leq m$, represents a marker. The order of the markers is also captured in the matrix, i.e., j'<j<j" if and only if marker j is located between markers j' and j" on the chromosome. A marker j is polymorphic if there exist progenies $i \neq i'$, such that $\mathcal{I} \neq \mathcal{I}$. In one embodiment, all the markers in $\mathcal{I}$ are considered to be polymorphic.

The jth marker of the ith progeny, also referred to as the position ⟨ij⟩, is $\mathcal{I}$ which is a pair of SNPs (single-nucleotide polymorphisms), or alternatively a pair of any other genomic markers with two possible values per position. Each individual SNP can be accessed as $\mathcal{I}(0)$ and $\mathcal{I}(1)$. Thus if $\mathcal{I} = \{A,C\}$ or simply written as AC, $\mathcal{I}(0)=A$ and $\mathcal{I}(1)=C$. When $\mathcal{I}(0)=\mathcal{I}(1)$, the position ⟨ij⟩ is said to be homozygous. Similarly, when $\mathcal{I}(0) \neq \mathcal{I}(1)$, the position ⟨ij⟩ is said to be heterozygous.

If $d_t$ is the true number of crossovers, then $0 \leq d_t \leq 2(m-1)n$ and an estimate $d_c \geq 0$ is a lower bound of $d_t$, if it is no larger than $d_t$. Consider a scenario where each position ⟨ij⟩ in $\mathcal{I}$ is heterozygous. In this case, the theoretical lower bound, on the number of crossovers in the unknown haplotypes of the progenies, is zero. Also there exists an exponentially large number ($2^{mn}$) of distinct equally-likely haplotype configurations of the progenies each with no crossover. While informative markers in general are chosen for their heterozygosity in data sets, it is observed that the same marker is also homozygous in many a progeny. Thus, in one embodiment, due to Mendelian inheritance, it is very unlikely to have a run of markers that are heterozygous in all the progenies. It is this random sprinkling of homozygous positions in $\mathcal{I}$ that makes estimation of a non-trivial lower bound possible.

Simulations were conducted to study the relationship between the lower bound estimate $d_c$ and extent of homozygosity in $\mathcal{I}$ in realistic data scenarios. For an algorithm-independent estimation of $d_c$ the following criteria was used for detectable crossovers. Let run r between ⟨ij⟨ and ⟩ij'⟩ be the sequence of entries of $\mathcal{I}$ in the row i, between columns j to j'. Further, r is a heterogenous run if it contains both homozygous and non-homozygous values. For progeny i, let $j_1 < j_2$ be such that there is no crossover at ⟨ij⟩ where $j_1 \leq j < j_2$ and at least one of ⟨$ij_1$⟨ and ⟩$ij_2$⟩ is a crossover position. Without loss of generality let $j_1$ be a position of crossover, then the crossover at ⟨$ij_1$⟩ is considered detectable if the run between ⟨$ij_1$⟩ and ⟨$ij_2$⟩ is heterogenous. Then the total number of detectable crossovers is $d_c$, the estimate on the lower bound.

Let e denote the mean number of crossovers in a progeny. Simulations were used with values $2 \leq e \leq 15$. It was observed that for this wide range of crossover profiles, the required fraction of homozygous sites in $\mathcal{I}$ to get a good estimate of $d_t$ (i.e., within 5% of the true value) was fixed. The empirical observation is summarized as follows: (Observation 1) When at least 28% of each subsample of randomly chosen positions in $\mathcal{I}$ is homozygous, the estimated lower bound $d_c$ is within 5% of the exact value $d_t$, i.e., $d_c \geq 0.95 d_t$.

In practice, values of n in the range of 50 to 400 and m in the range of 30 to 600 can be encountered. It has been consistently observed that at least 50% of the positions are homozygous and the solutions, obtained using methods discussed below, displayed $e \approx 2$. With a decrease in cost and an increase in accessibility of sequencing and genotyping technologies, m can be orders of magnitude larger in the near future. Note that e is not expected to increase with m. Thus, the lower bound estimation scales well with m, since the observation above is independent of m and the algorithm discussed in the later sections is linear in m.

Since each marker is bi-allelic, each column in $\mathcal{I}$ has no more than two distinct values. This can be seen in each column of the matrix shown in FIG. 3. Furthermore, the marker at each (yet unknown) haplotype of the progeny has two possible values. Let the two parents be denoted as a and b. Then the two distinct SNP values of parent p are represented by $V_j^p(0)$ and $V_j^p(1)$, p=a,b. Let Z and Z' be the two SNP values seen in the column j of $\mathcal{I}$, written as $\mathcal{I} = \{Z,Z'\}$. Then if Z=Z' then $V^a(k)=V^b(k)$, for k=0,1. Let $Z \neq Z'$. If there exists a progeny i with homozygous SNP Z, i.e., $\mathcal{I} = ZZ$, then $V_j^a(0)=V_j^b(0)=Z$. If there also exists some $i' \neq i$ such that $\mathcal{I} = Z'Z'Z'$, then $V_j^a(1)=V_j^b(1)=Z'$. Note that if there is no such i' then only one of $V^a(1)$ and $V^b(1)$ is Z' and the other is Z. Based on this, $\mathcal{I}$ is separated naturally into two matrices $M^a$ and $M^b$. For each i and j, and p=a,b, $$M_{ij}^p = \begin{cases} k & \text{if } \mathcal{I}_{ij}(0) = \mathcal{I}_{ij}(1) \text{ with } \mathcal{I}_{ij}(0) = V_j^p(k), \\ X & \text{if } \mathcal{I}_{ij}(0) \neq \mathcal{I}_{ij}(1). \end{cases} \quad \text{(EQ. 1)}$$

When each haplotype is expected to have exactly two founders then a represents one parent and b the other. This condition holds when all the progenies are crossed from exactly one pair of parents. In particular, for a crossed population, $V^a(0)$ encodes haplotype 0 of parent a and $V^a(1)$ encodes haplotype 1 of parent a. Similarly, $V^b(0)$ and $V^b(1)$. A lower bound computation also phases the parents a and b, through the appropriate updating of $V^p$, p=a,b.

FIG. 4 shows one example of $V^a$ and $V^b$ encodings based on the genotype data of FIG. 3. As can be seen, $V^a$ and $V^b$ are encoded to indicate the markers where each parent is heterozygous (X), where only one parent is heterozygous (x or x'), where one parent is homozygous (H), and where both parents are homozygous (h).

Let conjugate of z be written as $\tilde{z}$, where z is a matrix or a discrete value as defined below. Note that the conjugate of conjugate of z is z, i.e., $z=\tilde{\tilde{z}}$ always holds. For parents p=a,b, if p=a, then $\tilde{p}=b$ and vice-versa. Similarly, if k=0, then $\tilde{k}=1$ and vice-versa. Thus $M^a=\tilde{M}^b$ (and $M^b=\tilde{M}^a$). Also, $\tilde{V}^p(0)=V^p(1)$ and $\tilde{V}^p(1)=V^p(0)$ for the parents p=a,b. It should be noted that for readability purposes the superscript a (or b) from $M^a$ and $V^a$ (or $M^b$ and $V^b$) is removed wherever unambiguous. For a pair of markers j and j' four counts, $c_{k_1 k_2}$, $k_1,k_2=0,1$ are computed as:

$$c_{k_1 k_2} = |\{i | M_{ij}=k_1 \text{ and } M_{ij'}=k_2\}|.$$

Let the four counts in decreasing order be $c^1 \geq c^2 \geq c^3 \geq c^4$ and let $C_{jj'}=\{c^l|1\leq l\leq 4\}$. Without loss of generality, for each j, let $j_{n\times t}$ be the smallest j'>j such that $\Sigma_{c \in C_{jj'}} c > 0$. Let $xo(j, j_{n\times t})=c^3+c^4$. In fact, the minimal number of crossovers (or recombinations) between marker j and $j_{n\times t}$ is $xo(j, j_{n\times t})$. Moreover, the following is easily verified: (Observation 2) Given genotype data $\mathcal{I}$ on n progenies with m bi-allelic markers, the total number of crossovers in the progenies is $\geq \Sigma_{j=1}^m xo(j, j_{n\times t}) = d_c$.

In one embodiment, the lower bound can be improved by using appropriate threshold values at different stages. Thus, for a threshold, $thrsh_1=0.3n$, the marker $j_{n\times t}$ for a given j is such that the counts satisfy the condition $\Sigma c^l > thrsh_1$. This modified definition where $j'=j_{n\times t}$ is used in the following discussion. Further, when the quartet of counts $c^1$, $c^2$ and $c^3$, $c^4$ are well separated, i.e., $(c^3+c^4)/(c^1+c^2)<thrsh_2$, say with $thrsh_2=0.15$, then $C_{jj'}$ is referred to as being polarized. Let $\mathcal{I}=\{Z \not\approx Z'\}$. Then $\tilde{V}_j^p(1)$, p=a,b, can be computed based on the following observation: (Observation 3) If $C_{jj'}$ is not polarized, then $j \in J_p$ and $j' \in J_{\tilde{p}}$, for some p, where $J_p$ is the set of markers with exactly one heterozygous parent p.

After $V^p$ is updated each $M_{ij}^p \neq X$ is updated according to $V^p$ and each $M_{ij}^p=X$ based on $$M_{ij}^p \leftarrow \begin{cases} H & \text{if } V_j^p(0) = V_j^p(1), \\ k & \text{else if } V_j^{\tilde{p}}(k) \neq V_j^p(k) \text{ and } V_j^p(0) = V_j^p(1) \end{cases} \quad \text{(EQ. 2)}$$

Figures 5, 6:
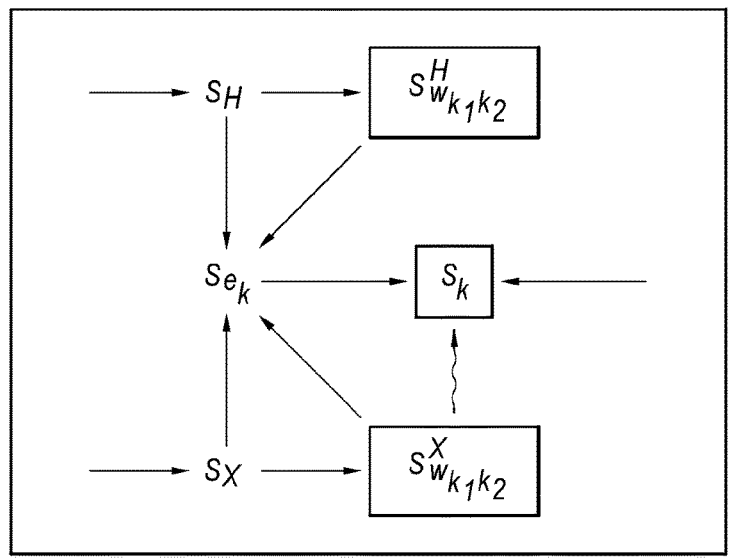
FIG. 5 shows one example of partially resolved haplotype sequences based on the encodings in FIG. 4 according to one embodiment of the present invention.
FIG. 6 illustrates permissible state transitions for haplotype matrices according to one embodiment of the present invention.

FIG. 5 shows one example of matrices $M^a$ and $M^b$ based on the encodings in $V^a$ and $V^b$ shown in FIG. 4 and EQ. 2 above.

For the pair of markers j and j', the two larger values ($c^1$ and $c^2$) are either $c_{00}$ and $c_{11}$ or $c_{01}$ and $c_{10}$. If $\{c^1,c^2\}=\{c_{01}, c_{10}\}$, then the values $V_j(0)$ and $V_j(1)$ are updated by interchanging them. Recall that the number of crossovers between j and j' is $\geq (c^3+c^4)$.

For the pair of markers j and j', $C_{jj'}$ must be polarized (Observation 4). Hence, when the quartet $c^1$, $c^2$ and $c^3$, $c^4$ is not polarized, then it is reasonable to assume significant experimental errors in the genotyping of marker j' (or j). To ensure that $V_{j'}$ is not updated multiple times, the reconstruction module 109 begins with the leftmost j where both $V_j$ are not homozygous. The marker j' is picked as above and then at the next stage j is assigned j' and the process continued until all j have been handled. In one embodiment, j' on the other side of j can be selected, while taking care not to update $V_{j'}$ multiple times. Furthermore, given $\mathcal{I}$, the haplotype matrices $M^a, M^b$ and the parent haplotypes $V^a, V^b$ can be constructed in $\mathcal{O}(mn)$ time (Observation 5).

It should be noted that sometimes there may be missing values in the data. When the value is missing at position $\langle ij \rangle$, the reconstruction module 109 makes the assignment $\mathcal{I} \leftarrow XX$. However, if after the computation of V, marker j is homozygous at parent p, then $M_{ij}^p \leftarrow H$ and $M_{ij}^{\tilde{p}}$ is appropriately updated. It can be verified that this treatment ensures that the estimated lower bound, $d_c$, is unaltered.

For selfed progenies, not only are the parents the same but even the haplotypes of the parents are deemed identical. Given selfed progenies, one of the following conditions holds for p=a,b and a numeric $k \in \{0,1\}$:

$V^a = V^b$ and if $M_{ij}^p=k$ then $M_{ij}^{\tilde{p}}=\tilde{k}$, for all i and j, or, (1)

$V^a \not\approx V^b$ and if $M_{ij}^p=k$ then $M_{ij}^{\tilde{p}}=k$, for all i and j. (2)

Measure of Uncertainty

In one embodiment, the reconstruction module 109 determines the preciseness of the output given a genotype matrix $\mathcal{I}$. This preciseness measurement is quantified by a triplet of measures $\Delta_\mathcal{I}$, $D_\mathcal{I}$, $E_\mathcal{I}$. $\Delta_\mathcal{I}$ is the deviation from the theoretical (algorithm-independent) lower bound. $D_\mathcal{I}$ is the extent of dispersion in position of each crossover. $E_\mathcal{I}$ is the error in the data. To compute these measures the reconstruction module 109 transforms the matrices $M^p$ as follows.

A parent, p, is homozygous at marker j when $V_j^p(0)=V_j^p(1)$ and is heterozygous otherwise. A position $\langle ij \rangle$ is a heterozygous trio, if the two parents at j are heterozygous and so is $\mathcal{I}$. Let k represent a numeric value and two functions $Lt(\bullet)$ and $Rt(\bullet)$ on an element of the matrix is defined as follows:

$$Lt(M_{ij}) = \begin{cases} k & \text{if } M_{ij'} = k \text{ for } 1 \leq j' < j, \text{ and there is no } j' < j'' < j \\ & \text{with numeric } M_{ij''}, \\ -1 & \text{otherwise.} \end{cases}$$

$$Rt(M_{ij}) = \begin{cases} k & \text{if } M_{ij'} = k \text{ for } j \leq j' < m, \text{ and there is no } j' > j'' > j \\ & \text{with numeric } M_{ij''}, \\ -1 & \text{otherwise.} \end{cases}$$

A set of transitions, $S_\_ \rightarrow S_\_$ that systematically transform the elements of M is now defined. Let $M_{ij}=x$. Then the transition $S_x \rightarrow S_\_$ is applied to assign the value y to $M_{ij}$ (written as $M_{ij} \leftarrow y$) as follows.

- $S_H \rightarrow S_{e_k}, S_X \rightarrow S_{e_k}$

If $Lt(M_{ij}) = Rt(M_{ij}) = k$, then $M_{ij} \leftarrow e_k$.

- $S_H \rightarrow S_{w_{k_1 k_2}}^H, S_X \rightarrow S_{w_{k_1 k_2}}^X$

If $Lt(M_{ij}) \neq Rt(M_{ij})$ with $Lt(M_{ij}) = k_1$ and $Rt(M_{ij}) = k_2$, then $M_{ij} \leftarrow w_{k_1 k_2}$.

- $S_{w_{k_1 k_2}}^X \rightarrow S_{e_k}, S_{w_{k_1 k_2}}^H \rightarrow S_{e_k}$ (note that $k_1 \neq k_2$)

If $Lt(M_{ij}) = Rt(M_{ij}) = k$, then $M_{ij} \leftarrow e_k$.

- $S_{e_k} \rightarrow S_k$ $M_{ij} \leftarrow k$.

- $S_{w_{k_1 k_2}}^X \rightarrow S_k$

If $\tilde{M}_{ij}$ is numeric, then $M_{ij} \leftarrow \tilde{V}(\tilde{M}_{ij})$.

In the above transitions $e_k$ is a temporary value in matrix M that is not present in the final version of M (i.e., matrix F discussed below). For example, $e_0$ at $M_{ij}$ denotes the case where the closest numerical value to the left and right of $M_{ij}$ is 0 (i.e. haplotype 0 spans over this marker at individual i). Eventually $e_k$ is stored as k in $M_{ij}$ [in the $S_{e_k} \rightarrow S_k$ transition]. Also, $w_{k_1 k_2}$ is a non-numerical value that can occur in the M and F matrices. The possible values are $w_{01}$ and $w_{10}$. For example, $w_{01}$ at $M_{ij}$ represents the case where the closest numerical value to the left of $M_{ij}$ is 0 and the closest numerical value to the right is 1 (there is a crossover at individual i whose location could be j). The values $w_{k_1 k_2}$ are considered in steps 3 and 4 (as non-numerical values in F) discussed below with respect to the agglomerate solution R.

To estimate the running time of the algorithm, the transitions are classified as intra-transitions and inter-transitions, depending on whether M or $\tilde{M}$ is used respectively. Thus, $$S^X_{w_{k_1 k_2}} \rightarrow S_k$$

is the only inter-transition. The above transitions are applied to the elements of $M^a$ and $M^b$ till no more transition is applicable. This final form of matrix is written as $F(M^a)$ or simply $F^a$. Similarly, $F(M^b)$ or simply $F^b$. The permissible transitions are captured in the transition diagram shown in FIG. 6. The three possible start states are $S_H$, $S_X$ and $S_k$, and the three possible final states are shown in boxes. The curly arrow represents the inter-transition while the straight arrows represent the intra-transitions. Note that each $M_{ij}$ undergoes no more than three transitions since there are no cycles in the state transition diagram. Also, each state with multiple outgoing edges has non-overlapping conditions, leading to a unique choice of transition.

Each element of $F^p$ is in the final state, i.e., for each position $\langle ij \rangle$, $F_{ij}^p \in \{0,1,w_{01},w_{10},-1\}$, p=a,b. A numeric value of −1 indicates that no information regarding the haplotypes can be deduced. The state transitions induce the following properties on F and V: (Observation 6) For a fixed i, the following hold:
(1) If $\tilde{F}_{ij}$ is not numeric but $F_{ij}$ is, then $V_j(0)=V_j(1)$ must hold.
(2) If $\tilde{F}_{ij}$ and $F_{ij}$ are both not numeric, then $\langle ij \rangle$, must be a heterozygous trio. The converse however is not true.
(3) If $F_{ij}=-1$, for some j, then $F_{ij}=\tilde{F}_{ij}=-1$, for all j.
(Observation 7)
(1) Given $M^a$ and $M^b$, $F^a$ and $F^b$ are unique.
(2) $F^a$ and $F^b$ can be constructed from $M^a$ and $M^b$ in $\mathcal{O}$(mn) time.

To show that $F^a$ and $F^b$ are unique, the iterations can be viewed as of two types: one where only inter-transitions and the other where only intra-transitions are applicable. In the very first iteration, due to the possible start states, no inter-transition can be applied. In the second iteration, where no intra-transition can be applied, the uniquely applicable inter-transitions are applied. Thus the iterations alternate between intra- and inter-transitions. Hence the final forms $F^a$ and $F^b$ are unique. Next, since each entry can go through no more than three transitions, it is possible to obtain $F^a$ and $F^b$ from $M^a$ and $M^b$ in $\mathcal{O}$(mn) time using suitable list data structures.

With respect to the agglomerate of feasible solutions, suppose there are L>0 feasible distinct solutions for a given $\mathcal{I}$. The reconstruction module 109, in one embodiment, generates an agglomerate in a single pair of matrices $R^a$ and $R^b$ that captures all the L solutions. The following illustrates one embodiment how the reconstruction module 109 constructs the agglomerate ($R^a$ and $R^b$) based on the encodings in $F^a$ and $F^b$ discussed above.

Let the conjugate of F be $\tilde{F}$ defined as $\tilde{F}^a=F^b$ and $\tilde{F}^b=F^a$. $R_{ij}^p$ that encodes all the possible solutions, is constructed from $F_{ij}^p$, p=a,b, as follows. New symbols *, q and Q are used in addition to the numeric values (0 and 1) in R. Also, for readability purposes the superscript a and b is removed, wherever unambiguous. For each progeny i:
1. If $F_{ij}=-1$ for some j, then without loss of generality $R_{ij} \leftarrow 0$ and $\tilde{R}_{ij} \leftarrow 1$, for all j.
2. If $F_{ij} \in \{0,1\}$, then $R_{ij} \leftarrow F_{ij}$.
3. For each j, if $\tilde{F}_{ij}$ is numeric and $F_{ij}$ is not, then $R_{ij} \leftarrow q$.
4. For each j, where $F_{ij}$ and $\tilde{F}_{ij}$ are both not numeric, then $$R_{ij} \atop \tilde{R}_{ij} \leftarrow \begin{cases} * & \text{if } V_j(0) = V_j(1), \\ q & \text{if } V_j(0) \neq V_j(1) = \tilde{V}_j(0) \ \& \ F_{ij} \neq \tilde{F}_{ij}, \\ q & \text{if } V_j(0) \neq V_j(1) = \tilde{V}_j(1) \ \& \ F_{ij} = \tilde{F}_{ij}, \\ Q & \text{otherwise}. \end{cases}$$

The non-numeric values in R encode multiple solutions, possibly with multiple crossovers, as discussed below.

With respect to the deviation from the lower bound $d_c$, let r be a run of contiguous values in a row (progeny) of R. Further, let r be maximal i.e., if r is non-numeric then it must be sandwiched on both sides by numeric values. Stated differently, if r is non-numeric the first and last non-numeric values of r are adjacent to a numeric value. Let $r^a$ and $r^b$ be the non-numeric runs in the two haplotypes of the progeny and are aligned in the examples discussed below. It is possible that only one of $r^a$ or $r^b$ is a numeric run, and this run is referred to as asymmetric. However, if both are non-numeric, then by construction $r^a=r^b$ and the run is symmetric. In the following discussion, the superscripts are removed, wherever unambiguous, for readability purposes.

A switch is defined to occur between q and Q or between Q and the numeric value that sandwiches the run. The number of switches is written as sw(r). The switch detection performed by the reconstruction module 109 is described by the following two examples. In the examples shown below, the run is represented by the non-numeric values in bold with numeric values to the left and right of the run. Each switch is marked as a numbered down-arrow.

In a first example (Example 1) consider the following run:
$r=r^a=r^b=$ . . . 000qqQQqqQQ111 . . .
The number of switches is 4 as shown:
. . . 000qq$\downarrow_1$QQ$\downarrow_2$qq$\downarrow_3$QQ$\downarrow_4$111 . . .
The value * is a wild card and can be treated either as q or Q. Thus, the wild card may result in different positions of the same switch.

In a second example (Example 2) the following run has three wild cards:
$r=r^a=r^b=$ . . . 000q*qQ*QQqq*Q111 . . .
The first wild card is treated as a q, the second wild card is treated as a Q, and the third wild card can be treated as a q or Q with two possible positions for the third switch.
. . . 000q*q$\downarrow_1$Q*QQ$\downarrow_2$qq$\downarrow_3$*$\downarrow_3$,Q$\downarrow_4$111 . . .
The wild card counts of the four switches are 1, 1, 2, and 1 respectively.

When sw(r)>0, the location of the switches in the run r may define additional positions $\langle ij \rangle$ in R that can updated from non-numeric to numeric. These are the positions that are to the left of the leftmost switch and to the right of the rightmost switch positions. Thus, the run of Example 1 is transformed where the length of the non-numeric run shrinks from 8 to 6.

$$...000qq\downarrow_1 QQ\downarrow_2 qq\downarrow_3 QQ\downarrow_4 111...$$

$$...00000\downarrow_1 QQ\downarrow_2 qq\downarrow_3 QQ\downarrow_4 111...$$

Similarly the length of run of Example 2 shrinks from 11 to 9.

$$...000q*q\downarrow_1 Q*QQ\downarrow_2 qq\downarrow_3 *\downarrow_{3'} Qred\downarrow_4 111...$$
$$\Downarrow$$
$$...000000\downarrow_1 Q*QQ\downarrow_2 qqd\downarrow_3 *\downarrow_{3'} Q\downarrow_4 111...$$

The transformed values are shown in bold numeric values above. The same process is applied to every non-numeric run r to transform the matrices $R^a$ and $R^b$.

Then (Observation 8) R is such that for each non-numeric run r, if sw(r)>0, then (1) r begins and ends with Q and (2) the positions of the first and the last switch sandwich the non-numeric run. To summarize: (Observation 9) Let r be a non-numeric run and let s=sw(r). Then (1) the total number of crossovers in the run, across both the haplotypes, is exactly s and each crossover in each haplotype of the configuration is at a position of the switch. (2) If r is an asymmetric run, s is zero. In general, s is even and the number of crossovers in each haplotype of each distinct configuration is odd. However, is this not a requirement.

(Observation 10) Let s=sw(r) for a non-numeric run r. Then if s≤2, there is no additional crossover introduced by r. If s>2, the number of additional crossovers is s−2. Let U be the set of all maximal non-numeric runs in R. Then if $\Delta_\mathcal{I}$ denotes the deviation from the lower bound, $d_c$, the reconstruction module 109 calculates $\Delta_\mathcal{I}$ as $$\Delta_\mathcal{I} = \sum_{r \in U} |sw(r) - 2|.$$

Regarding the dispersion index and error estimate, the dispersion index, $D_\mathcal{I}$, is a measure of the uncertainty in the position of the crossovers. This is computed by the reconstruction module 109 as an average over all predicted crossovers. Thus, $$D_\mathcal{I} = \frac{\sum_{r \in U} \delta(r)}{(m-1)(d_c + \Delta_\mathcal{I})},$$

where $$\delta(r) = \begin{cases} len(r)+1 & \text{if } sw(r)=0, \\ \sum_l 2c_l & \text{otherwise } (c_l \text{ is the wild card count of each switch } l \text{ in } r). \end{cases}$$

When the location of each crossover is known precisely, this index is 0. A value of 1 indicates maximum uncertainty in the location.

If $R_{ij}, \tilde{R}_{ij} \in \{0,1\}$, then the position ⟨ij⟩ has a mismatch if $\{V(R_{ij}), \tilde{V}(\tilde{R}_{ij})\} \neq \mathcal{I}$. Note that the mismatch at this position could be flagged as an error or one of $R_{ij}$ and $\tilde{R}_{ij}$ can be modified to potentially introduce additional crossover(s). These are undetectable during the lower bound computation and do not overlap with the non-numeric regions. Let N be the number of such mismatches. Then, $E_\mathcal{I}$, which is the error estimate in $\mathcal{I}$ calculated by the reconstruction module 109, is defined as N/mn. In most instances the number of mismatches is very low (less than 0.01%) and the mismatches are experimental errors. Hence, the convention that such a mismatch be flagged as a potential error has been followed in one embodiment. Then, an error, if any, is at ⟨ij⟩ in F that underwent the transitions $S_X \to \ldots S_{e_k} \to S_k$. Note that the converse is not true. Also, an additional crossover, if any, is at ⟨ij⟩ in F that underwent the transitions $$S_X \to S^X_{w_{k_1 k_2}}.$$

Again, the converse is not true. To summarize, the trio ($\Delta_\mathcal{I}$, $D_\mathcal{I}$, $E_\mathcal{I}$) define the uncertainty in the solution of the genotypes $\mathcal{I}$.

Haplotype Frequency Distributions

One of the important consequences of haplotype inferencing is the haplotype frequency distribution across the chromosomes. A marker j of progeny i has two SNPs, one derived either from haplotype 0 or haplotype 1 of parent a and the other either from haplotype 0 or haplotype 1 of parent b. Since R is an agglomerate data structure and also contains the non-numeric values that encode multiple configurations. Based on the encoding in R the reconstruction module 109 estimates the expected value of the frequency count and its variance. First, the reconstruction module enumerates the feasible solutions encoded by a non-numeric run r. For example, consider the following example (Example 3) where in each of the following the length of the run, len(r), is 3 and the number of additional crossovers is zero. However, the number of configurations is different based on the structure of the switches.

Two runs with sw(r)=0 each:

$$r^a = ...00qqq111...$$
$$r^b = ...11qqq000...$$
or
$$r^a = ...00***111...$$
$$r^b = ...11***000...$$
$$\Leftrightarrow \begin{cases} ...00|111111... \\ ...11|000000... \\ \text{or} \\ ...000|11111... \\ ...111|00000... \\ \text{or} \\ ...0000|1111... \\ ...1111|0000... \\ \text{or} \\ ...00000|111... \\ ...11111|000... \end{cases}$$

A run with sw(r)=2:

$$\left.\begin{array}{l} r^a = ...00QQQ111... \\ r^b = ...11QQQ000... \\ \Updownarrow \\ ...00\downarrow_1 QQQ\downarrow_2 111... \end{array}\right\} \Leftrightarrow \begin{cases} ...00|_1 111111... \\ ...11111|_2 000... \\ \text{or} \\ ...11111|_2 000... \\ ...00|_1 111111... \end{cases}$$

The 8 distinct configurations for Example 1 discussed above are:

```
... 00000|₁ 111111111 ...
... 0000000|₂ 11|₃ 00|₄ 111 ...
or
... 0000000|₂ 1111111 ...
... 00000|₁ 1111|₃ 00|₄ 111 ...
or
... 000000000|₃ 11111 ...
... 00000|₁ 11|₂ 0000|₄ 111 ...
or
... 00000000000|₄ 111 ...
... 00000|₁ 11|₂ 00|₄ 11111 ...
or
... 0000000|₂ 11|₃ 00|₄ 111 ...
... 00000|₁ 111111111 ...
or
... 00000|₁ 1111|₃ 00|₄ 111 ...
... 0000000|₂ 1111111 ...
or
... 00000|₁ 11|₂ 0000|₄ 111 ...
... 000000000|₃ 11111 ...
or
... 00000|₁ 11|₂ 00|₃ 11111 ...
... 00000000000|₄ 111 ...
```

Let $wt(r)$ be the number of distinct solutions encoded by r. (Observation 11) Let $s=sw(r)$ for a run r. Let $c_1, c_2, \ldots c_s$ be the wild card counts of the switch positions. Let $wt(r)$ be the number of distinct feasible solutions due to r. Then (1) If $s < 2$, $wt(r) = len(r + 1)$. (EQ. 3)

(2) If $s \geq 2$, $wt(r) = Z(r) \prod_{l=1}^{s} c_l$, where $$Z(r) = 2\left(\sum_{l=1}^{\lceil s/4 \rceil - 1} \binom{s}{2l-1}\right) + \binom{s}{2\lceil s/4 \rceil - 1}.$$

EQ. 3 is explained through the following example (Example 4). Consider the following r with $sw(r)=6$:

000QqQqQ111 ⇒ 000←₁Q←₂q←₃Q←₄q←₅Q←₆111

Note that the 6 switches can be shared by the two haplotypes as 1 and 5 (the first column), or as 3 and 3 (second column) as follows.

```
000 |₁ 11111111        000 |₁ 1 |₂ 0 |₃ 11111
0000 |₂ 1 |₃ 0 |₄ 1 |₅ 0 |₆ 111   000000 |₄ 1 |₅ 0 |₆ 111
       or                       or
000 |₂ 1111111        000 |₁ 111 |₄ 00 |₆ 111
000 |₁ 11 |₃ 0 |₄ 1 |₅ 0 |₆ 111   0000 |₂ 1 |₃ 00 |₅ 1111
       or                       or
       ⋮                        ⋮
```

There are six distinct configurations for the first case and since the two haplotypes can be switched it gives 2×6 distinct configurations. For the second there are $$\binom{6}{3} = 20$$

distinct configuration, giving a total of 12+20 distinct solutions due to r.

Based on R, the reconstruction module 109 estimates the expected value of the frequency count of the haplotype pairs and its variance. If $R_{ij}$ is non-numeric, let $R_{ij}=\alpha$ hold. Thus, for each marker j consider the following, for x, y=0,1,α, $$c_{xy} = |\{i | R_{ij}{}^a = x \text{ and } R_{ij}{}^b = y\}|$$

In the absence of any other external information, each of the alternative solutions in R is equally likely. Under this assumption, the expected count, $\hat{c}_{k_1 k_2}$, of each haplotype pair, $k_1, k_2 = 0,1$, is estimated as follows:

$$\hat{c}_{k_1 k_2} = c_{k_1 k_2} + \Delta_{k_1 k_2}, \text{ where}$$

$$\Delta_{k_1 k_2} = c_{\alpha k_2}/2 + c_{k_1 \alpha}/2 + c_{\alpha \alpha}/4.$$

Further, the variance $\sigma_{k_1, k_2}{}^2$ of the count of the haplotype pair is approximated as $\Delta_{k_1 k_2}$.

It should be noted that the reconstruction module 109, in one embodiment, outputs the equally-likely solutions in R as well as the haplotype distribution and variance information to a user. Additionally, the reconstruction module 109 can visualize the solutions as mosaics of the ancestor haplotypes. This information can be output to a display where the user can interact with the information.

Operational Flow Diagrams

Figure 7:
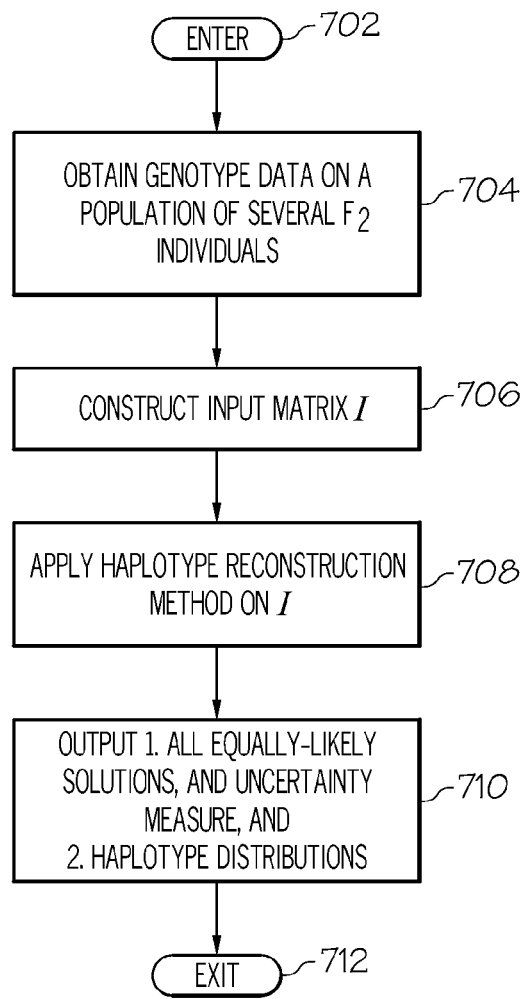
FIG. 7 is an operational flow diagram illustrating one example of a process for reconstructing haplotypes from genotype data according to one embodiment of the present invention.

FIG. 7 is an operational flow diagram illustrating one example of an overall process for reconstructing haplotypes from genotype data. The operational flow diagram begins at step 702 and flows directly to step 704. The reconstruction module 109, at step 704, obtains genotype data on a population of several F2 individuals. The reconstruction module 109, at step 706, constructs an input matrix $\mathcal{I}$ from the genotype data. The reconstruction module 109, at step 708, performs the haplotype reconstruction operations discussed above. The reconstruction module 109, at step 710, outputs all equally-likely solutions along with an uncertainty measure (i.e. a preciseness of the agglomerate data structure in terms of statistical measures) and haplotype distributions. This information can be used to study statistical trends such as haplotype distribution along chromosomes to, for example, observe biases. This information can also be used to hand-pick individuals based on their observed recombinations for further examination. It should be noted that other analyses can be performed on this information as well. The control flow exits at step 712.

Figure 8:
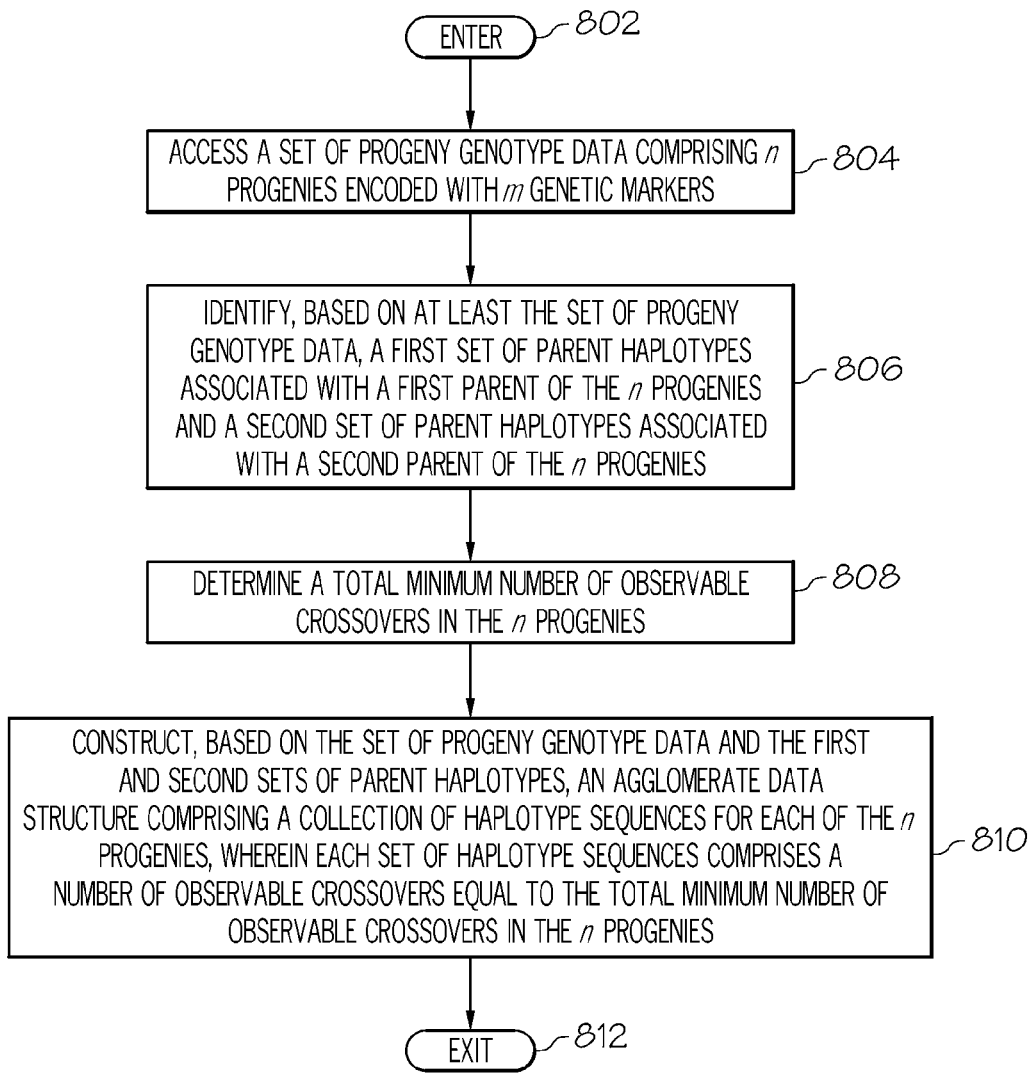
FIG. 8 is an operational flow diagram illustrating another example of a process for reconstructing haplotypes from genotype data according to one embodiment of the present invention.

FIG. 8 is an operational flow diagram illustrating another example of a process for reconstructing haplotypes from genotype data. The operational flow diagram begins at step 802 and flows directly to step 804. The reconstruction module 109, at step 804, accesses a set of progeny genotype data comprising n progenies encoded with m genetic markers. Each of the m genetic markers comprises two values. Also, a combination of each of the m genetic markers associated with a progeny represents a genotype sequence of the progeny. The reconstruction module 109, at step 806, identifies, based on at least the set of progeny genotype data, a first set of parent haplotypes associated with a first parent of the n progenies and a second set of parent haplotypes associated with a second parent of the n progenies. The reconstruction module 109, at step 808, determines a total minimum number of observable crossovers in the n progenies. The reconstruction module 109, at step 810, constructs, based on the set of progeny genotype data and the first and second sets of parent haplotypes, an agglomerate data structure comprising a collection of a set of haplotype sequences characterizing the n progenies in terms of the first and second sets of parent haplotypes. Each set of haplotype sequences comprises a number of observable crossovers equal to the total minimum number of observable crossovers in the n progenies. The control flow exits at step 812.

NON-LIMITING EXAMPLES

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention have been discussed above with reference to flowchart illustrations and/or block diagrams of methods, apparatus (systems) and computer program products according to various embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A system for generating an agglomerate data structure that reduces computation time of one or more information processing systems when reconstructing haplotypes from genotype data in a model-free setting, the system comprising:
 a memory;
 a processor communicatively to the memory; and
 a reconstruction circuit communicatively coupled to the memory and processor, the reconstruction circuit:
  electronically communicating with at least one external information processing system;
  electronically receiving, based on electronically communicating with the at least one external information processing system, a set of progeny genotype data, the set of progeny genotype data comprising n progenies encoded with m biallelic genetic markers, where each of the n progenies are full siblings, wherein each of the m biallelic genetic markers comprises two values, and wherein a combination of each of the m biallelic genetic markers associated with a progeny represents a genotype sequence of the progeny comprising at least a chromosome segment;
  constructing, by based on the set of progeny genotype data, an agglomerate data structure comprising a collection of sets of haplotype sequences characterizing the n progenies in terms of first and second sets of parent haplotypes, wherein each set of haplotype sequences comprises a number of observable crossovers equal to the total minimum number of observable crossovers in the n progenies;
  reducing computation time of the one or more information processing systems when reconstructing haplotypes from genotype data in a model-free setting by constructing the agglomerate data structure in linear time, wherein constructing the agglomerate data structure in linear time comprises:
   electronically transforming the set of progeny genotype data into a data structure, the data structure encoding the set of progeny genotype data where the encoding represents each of n progenies in the set of progeny genotype data as one row in a plurality of rows of the data structure and represents each of m biallelic genetic markers in the set of progeny genotype data as one column in a plurality of columns of the data, wherein the encoding further orders the plurality of columns corresponding to an order of the m biallelic genetic markers;
   electronically accessing the set of progeny genotype data within the data structure;
   identifying, based on electronically accessing the set of progeny genotype data, a first set of parent haplotypes associated with a first parent of the n progenies and a second set of parent haplotypes associated with a second parent of the n progenies, the identifying comprising
    splitting the data structure into a first parental data structure and a second parental data structure by transforming a set of data representing genetic contributions for each of a first parent and a second parent of the n progenies and inferring any missing genotype data for one or more of at least one of the n progenies parents, the first parent, or the second parent wherein the transforming comprises utilizing a set of monotonic state transitions that systematically transform the set of data into the first parental data structure and the second parental data structure each comprising different data than the set of data, wherein the first parental data structure encodes haplotypes of a first parent of the n progenies and the second parental data structure encodes haplotypes of a second parent of the n progenies, where the first set of parent haplotypes is identified from the first parental data structure and the second set of parent haplotypes is identified from the second parental data structure;
   determining a total minimum number of observable crossovers in the n progenies based on data within the first parental data structure and a second parental data structure;
   constructing, based on the set of progeny genotype data and the first and second sets of parent haplotypes, the agglomerate data structure comprising a collection of sets of haplotype sequences characterizing the n progenies in terms of the first and second sets of parent haplotypes, wherein each set of haplotype sequences comprises a number of observable crossovers equal to the total minimum number of observable crossovers in the n progenies; and
  programming a processor of at least one information processing system utilizing the collection of sets of haplotype sequences from the agglomerate data structure to at least
   analyze statistical trends regarding haplotype distribution along chromosomes to observe biases, and determine a specific form of a gene that is associated with disease susceptibility.

2. The system of claim 1, wherein the method further comprises:
 determining a preciseness of the agglomerate data structure in terms of statistical measures.

3. The system of claim 1, wherein the data structure is a matrix I comprising rows i and columns j, wherein each row i, $1 \leq i \leq n$ represents a progeny in the n progenies and each column j, $1 \leq j \leq m$ represents a marker in the m biallelic genetic markers
 splitting the first data structure comprises:
 constructing matrices $M_{ij}^p$, where $$M_{ij}^p = \begin{cases} k & \text{if } I_{ij}(0) = I_{ij}(1) \text{ with} \\ & I_{ij}(0) = V_j^p(k), \\ X & \text{if } I_{ij}(0) \neq I_{ij}(1) \end{cases}$$

where p=a, b, and a and b are distinct parents, wherein two distinct marker values of parent p at column j are represented by $V_j^p(0)$ and $V_j^p(1)$, and where Z and Z' are the two values of the marker in column j of I, and if Z=Z' then $V^a(k)=V^b(k)$, for k=0,1, when Z≠Z' and there exists a progeny i with homozygous marker Z, then $V_j^a(0)=V_j^b(0)=Z$, if there also exists some i'≠i where I=Z'Z', then $V_j^a(1)=V_j^b(1)=Z'$, and if there is no such i' then only one of $V^a(1)$ and $V^b(1)$ is Z' and the other is Z.

4. The system of claim 3, wherein $V_j^p(1)$, p=a,b, is computed based on $j \in J_p$ and $j' \in J_p$, for some p, where $J_p$ is a set of markers with exactly one heterozygous parent, where for parents p=a,b, if p=a, then p=b and vice-versa, and where, if k=0, then $\tilde{k}$=1 and vice-versa, and where $M^a$=$\tilde{M}^b$ (and $M^b$=$\tilde{M}^a$), and, $V^p(0)=V^p(1)$ and $V^p(1)=V^p(0)$ for parents p=a,b.

5. The system of claim of 4, further comprising updating each $M_{ij}^p \neq X$ according to $V^p$ and each $M_{ij}^p=X$ based on $$M_{ij}^p \leftarrow \begin{cases} H & \text{if } V_j^p(0) = V_j^p(1), \\ k & \text{else if } V_j^p(k) \neq V_j^p(\tilde{k}) \text{ and } V_j^p(0) = V_j^p(1) \end{cases}$$

where, a pair of markers j and j' are polarized, and for the pair of markers j and j' a set of two counts $c^1$ and $c^2$ are one of $c_{00}$ and $c_{11}$ or $c_{01}$ and $c_{10}$, and if $\{c^1,c^2\}=\{c_{01}, c_{10}\}$, then values $V_j(0)$ and $V_j(1)$ are updated by interchanging them.

6. The system of claim 5, wherein the method further comprises:
transforming each of the updated matrices $M_{ij}^p$ to $F(M^a)$ and $F(M^b)$, respectively, using a set of monotonic state transitions based on functions $Lt(M_{ij})$ and $Rt(M_{ij})$, where $$Lt(M_{ij}) = \begin{cases} k & \text{if } M_{ij'} = k \text{ for } 1 \leq j' < j, \\ & \text{and there is no } j' < j'' < j \\ & \text{with numeric } M_{ij''}, \\ -1 & \text{otherwise} \end{cases}$$

$$Rt(M_{ij}) = \begin{cases} k & \text{if } M_{ij'} = k \text{ for } j \leq j' < m, \\ & \text{and there is no } j' > j'' > j \\ & \text{with numeric } M_{ij''}, \\ -1 & \text{otherwise} \end{cases}$$

where, for a fixed i,
if $F_{ij}$ is not numeric but $F_{ij}$ is, then, $V_j(0)=V_j(1)$
if $F_{ij}$ and $F_{ij}$ are both not numeric, then $\langle ij \rangle$, is a heterozygous trio,
if $F_{ij}=-1$, for some j, then $F_{ij}=F_{ij}=-1$, for all j, and
wherein $F(M^a)$ and $F(M^b)$ are constructed from $M_{ij}^a$ and $M_{ij}^b$ in O(mn) time,
wherein constructing the agglomerate data structure comprising the set of haplotype sequences comprises:
generating an agglomerate of the set of haplotype sequences in a single pair of matrices $R_{ij}^p$, wherein p=a, b, from $F(M^a)$ and $F(M^b)$.

7. The system of claim 6, wherein $R_{ij}^p$ is generated based on, for each progeny i:
if $F_{ij}=-1$ for some j, then $R_{ij} \leftarrow 0$ and $R_{ij} \leftarrow 1$, for all j;
if $F_{ij} \in \{0,1\}$, then $R_{ij} \leftarrow F_{ij}$;
for each j, if $F_{ij}$ is numeric and $F_{ij}$ is not, then $R_{ij} \leftarrow q$; and
for each j, where $F_{ij}$ and $F_{ij}$ are both not numeric, then $$\begin{matrix} R_{ij}, \\ \tilde{R}_{ij} \end{matrix} \leftarrow \begin{cases} * & \text{if } V_j(0) = V_j(1), \\ q & \text{if } V_j(0) \neq V_j(1) = V_j(0) \text{ \& } F_{ij} \neq F_{ij}, \\ q & \text{if } V_j(0) \neq V_j(1) = V_j(1) \text{ \& } F_{ij} = F_{ij}, \\ Q & \text{otherwise} \end{cases}$$

where non-numeric values in $R_{ij}^p$ encode multiple solutions.

8. The system of claim 7, wherein the method further comprises:

determining an error estimate $E_1$ in I as N/mn, where N is a number of genotype data mismatches in $R_{ij}^p$, where a position $\langle ij \rangle$ has a mismatch if $\{V(R_{ij}), \tilde{V}(R_{ij})\} \neq I_{ij}$ and $R_{ij}, \tilde{R}_{ij} \in \{0,1\}$.

9. The system of claim of claim 7, wherein the method further comprises:
determining a haplotype frequency distribution for the collection of the set of haplotype sequences in the agglomerate data structure, wherein the determining is based on
$k_1, k_2=0,1$ being a haplotype pair, and
if $R_{ij}$ is non-numeric, let $R_{ij}=\alpha$ hold, where for each marker j for $x,y=0,1,\alpha$, $c_{xy}=|\{i | R_{ij}^a=x \text{ and } R_{ij}^b=y\}|$, and an expected count $\hat{c}_{k_1k_2}$ of each haplotype pair is $\hat{c}_{k_1k_2}=c_{k_1k_2}+\Delta_{k_1k_2}$ where $\Delta_{k_1k_2}=c_{\alpha k_2}/2+c_{k_1\alpha}/2+c_{\alpha\alpha}/4$.

10. The system of claim 9, wherein the method further comprises:
determining a variance $\sigma_{k_1k_2}^2$ of haplotype frequency distribution as $\Delta_{k_1k_2}$.

11. A computer program storage product for generating an agglomerate data structure that reduces computation time of one or more information processing systems when reconstructing haplotypes from genotype data in a model-free setting, the computer program storage product comprising instructions configured to perform a method comprising:
electronically communicating with at least one external information processing system;
electronically receiving, based on electronically communicating with the at least one external information processing system, a set of progeny genotype data, the set of progeny genotype data comprising n progenies encoded with m biallelic genetic markers, where each of the n progenies are full siblings, wherein each of the m biallelic genetic markers comprises two values, and wherein a combination of each of the m biallelic genetic markers associated with a progeny represents a genotype sequence of the progeny comprising at least a chromosome segment;
constructing, by based on the set of progeny genotype data, an agglomerate data structure comprising a collection of sets of haplotype sequences characterizing the n progenies in terms of first and second sets of parent haplotypes, wherein each set of haplotype sequences comprises a number of observable crossovers equal to the total minimum number of observable crossovers in the n progenies;
reducing computation time of the one or more information processing systems by constructing the agglomerate data structure in linear time, wherein constructing the agglomerate data structure in linear time comprises:
electronically transforming the set of progeny genotype data into a data structure, the data structure encoding the set of progeny genotype data where the encoding represents each of n progenies in the set of progeny genotype data as one row in a plurality of rows of the data structure and represents each of m biallelic genetic markers in the set of progeny genotype data as one column in a plurality of columns of the data, wherein the encoding further orders the plurality of columns corresponding to an order of the m biallelic genetic markers;
electronically accessing the set of progeny genotype data within the data structure;
identifying, based on electronically accessing the set of progeny genotype data, a first set of parent haplotypes associated with a first parent of the n progenies and a second set of parent haplotypes associated with a second parent of the n progenies, the identifying comprising splitting the data structure into a first parental data structure and a second parental data structure by transforming a set of data representing genetic contributions for each of a first parent and a second parent of the n progenies and inferring any missing genotype data for one or more of at least one of the n progenies parents, the first parent, or the second parent wherein the transforming comprises utilizing a set of monotonic state transitions that systematically transform the set of data into the first parental data structure and the second parental data structure each comprising different data than the set of data, wherein the first parental data structure encodes haplotypes of a first parent of the n progenies and the second parental data structure encodes haplotypes of a second parent of the n progenies, where the first set of parent haplotypes is identified from the first parental data structure and the second set of parent haplotypes is identified from the second parental data structure;

determining a total minimum number of observable crossovers in the n progenies based on data within the first parental data structure and a second parental data structure;

constructing, based on the set of progeny genotype data and the first and second sets of parent haplotypes, the agglomerate data structure comprising a collection of sets of haplotype sequences characterizing the n progenies in terms of the first and second sets of parent haplotypes, wherein each set of haplotype sequences comprises a number of observable crossovers equal to the total minimum number of observable crossovers in the n progenies; and programming a processor of at least one information processing system utilizing the collection of sets of haplotype sequences from the agglomerate data structure to at least analyze statistical trends regarding haplotype distribution along chromosomes to observe biases, and determine a specific form of a gene that is associated with disease susceptibility.

12. The computer program storage product of claim 11, wherein the method further comprises:

determining a preciseness of the agglomerate data structure in terms of statistical measures.

13. The computer program storage product of claim 11, wherein the data structure is a matrix I comprising rows i and columns j, wherein each row i, $1 \leq i \leq n$ represents a progeny in the n progenies and each column j, $1 \leq j \leq m$ represents a marker in the m biallelic genetic markers wherein splitting the first data structure comprises:

constructing matrices $M_{ij}^p$, where $$M_{ij}^p = \begin{cases} k & \text{if } I_{ij}(0) = I_{ij}(1) \text{ with} \\ & I_{ij}(0) = V_j^p(k), \\ X & \text{if } I_{ij}(0) \neq I_{ij}(1) \end{cases}$$

where p=a, b, and a and b are distinct parents, wherein two distinct marker values of parent p at column j are represented by $V_j^p(0)$ and $V_j^p(1)$, and where Z and Z' are the two values of the marker in column j of I, and if Z=Z' then $V^a(k)=V^b(k)$, for k=0,1, when Z≠Z' and there exists a progeny i with homozygous marker Z, then $V_j^a(0)=V_j^b(0)=Z$, if there also exists some i'≠i where I=Z'Z', then $V_j^a(1)=V_j^b(1)=Z'$, and if there is no such i' then only one of $V^a(1)$ and $V^b(1)$ is Z' and the other is Z.

14. The computer program storage product of claim 13, wherein $V_j^p(1)$, p=a,b, is computed based on $j \in J_p$ and $j' \in J_p$, for some p, where $J_p$ is a set of markers with exactly one heterozygous parent, where for parents p=a,b, if p=a, then p=b and vice-versa, and where, if k=0, then k=1 and vice-versa, and where $M^a = \tilde{M}^b$ (and $M^b = \tilde{M}^a$), and, $V^p(0)=V^p(1)$ and $V^p(1)=V^p(0)$ for parents p=a,b.

15. The computer program storage product of claim of 14, further comprising updating each $M_{ij}^p \neq X$ according to $V^p$ and each $M_{ij}^p = X$ based on $$M_{ij}^p \leftarrow \begin{cases} H & \text{if } V_j^p(0) = V_j^p(1), \\ k & \text{else if } V_j^p(k) \neq V_j^p(k) \text{ and } V_j^p(0) = V_j^p(1) \end{cases}$$

where, a pair of markers j and j' are polarized, and for the pair of markers j and j' a set of two counts $c^1$ and $c^2$ are one of $c_{00}$ and $c_{11}$ or $c_{01}$ and $c_{10}$, and if $\{c^1,c^2\}=\{c_{01},c_{10}\}$, then values $V_j(0)$ and $V_j(1)$ are updated by interchanging them.

16. The computer program storage product of claim 15, wherein the method further comprises:

transforming each of the updated matrices $M_{ij}^p$ to $F(M^a)$ and $F(M^b)$, respectively, using a set of monotonic state transitions based on functions $Lt(M_{ij})$ and $Rt(M_{ij})$, where $$Lt(M_{ij}) = \begin{cases} k & \text{if } M_{ij'} = k \text{ for } 1 \leq j' < j, \\ & \text{and there is no } j' < j'' < j \\ & \text{with numeric } M_{ij''}, \\ -1 & \text{otherwise} \end{cases}$$

$$Rt(M_{ij}) = \begin{cases} k & \text{if } M_{ij'} = k \text{ for } j \leq j' < m, \\ & \text{and there is no } j' > j'' > j \\ & \text{with numeric } M_{ij''}, \\ -1 & \text{otherwise} \end{cases}$$

where, for a fixed i, if $F_{ij}$ is not numeric but $F_{ij}$ is, then, $V_j(0)=V_j(1)$ if $F_{ij}$ and $F_{ij}$ are both not numeric, then $\langle ij \rangle$, is a heterozygous trio, if $F_{ij}=-1$, for some j, then $F_{ij}=F_{ij}=-1$, for all j, and wherein $F(M^a)$ and $F(M^b)$ are constructed from $M_{ij}^a$ and $M_{ij}^b$ in O (mn) time, wherein constructing the agglomerate data structure comprising the set of haplotype sequences comprises:

generating an agglomerate of the set of haplotype sequences in a single pair of matrices $R_{ij}^p$, wherein p=a, b, from $F(M^a)$ and $F(M^b)$.

17. The computer program storage product of claim 16, wherein $R_{ij}^p$ is generated based on, for each progeny i:

if $F_{ij}=-1$ for some j, then $R_{ij} \leftarrow 0$ and $R_{ij} \leftarrow 1$, for all j;

if $F_{ij} \in \{0,1\}$, then $R_{ij} \leftarrow F_{ij}$;

for each j, if $F_{ij}$ is numeric and $F_{ij}$ is not, then $R_{ij} \leftarrow q$; and for each j, where $F_{ij}$ and $F_{ij}$ are both not numeric, then $$R_{ij}, \tilde{R}_{ij} \leftarrow \begin{cases} * & \text{if } V_j(0) = V_j(1), \\ q & \text{if } V_j(0) \neq V_j(1) = V_j(0) \text{ \& } F_{ij} \neq F_{ij}, \\ q & \text{if } V_j(0) \neq V_j(1) = V_j(1) \text{ \& } F_{ij} = F_{ij}, \\ Q & \text{otherwise} \end{cases}$$

where non-numeric values in $R_{ij}^p$ encode multiple solutions.

18. The computer program storage product of claim 17, wherein the method further comprises:

determining an error estimate $E_I$ in I as N/mn, where N is a number of genotype data mismatches in $R_{ij}^p$, where a position $\langle ij \rangle$ has a mismatch if $\{V(R_{ij}), V(\tilde{R}_{ij})\} I_{ij}$ and $R_{ij}, \tilde{R}_{ij} \in \{0,1\}$.

19. The computer program storage product of claim of claim 17, wherein the method further comprises:

determining a haplotype frequency distribution for the collection of the set of haplotype sequences in the agglomerate data structure, wherein the determining is based on $k_1, k_2 = 0, 1$ being a haplotype pair, and if $R_{ij}$ is non-numeric, let $R_{ij} = \alpha$ hold, where for each marker j for x,y=0,1,$\alpha$, $c_{xy} = |\{i | R_{ij}^\alpha = x \text{ and } R_{ij}^b = y\}|$, and an expected count $\hat{c}_{k_1 k_2}$ of each haplotype pair is $\hat{c}_{k_1 k_2} = c_{k_1 k_2} \Delta_{k_1 k_2}$, where $\Delta_{k_1 k_2} = c_{\alpha k_2}/2 + c_{k_1 \alpha}/2 + c_{\alpha \alpha}/4$.

20. The computer program storage product of claim 19, wherein the method further comprises:

determining a variance $\sigma_{k_1, k_2}^2$ of haplotype frequency distribution as $\Delta_{k_1 k_2}$.

\* \* \* \* \*